United States Patent
Singh et al.

(10) Patent No.: US 9,734,316 B2
(45) Date of Patent: Aug. 15, 2017

(54) SYSTEM AND METHOD FOR DETECTING LIVENESS DURING BIOMETRIC AUTHENTICATION

(71) Applicant: Wipro Limited, Bangalore (IN)

(72) Inventors: Karan Singh, Sri Ganganagar (IN); Akshit Singhvi, Udaipur (IN); Vinod Pathangay, Bangalore (IN)

(73) Assignee: WIPRO LIMITED, Bangalore (IN)

(*) Notice: Subject to any disclaimer, the term of this patent is extended or adjusted under 35 U.S.C. 154(b) by 0 days.

(21) Appl. No.: 14/829,055

(22) Filed: Aug. 18, 2015

(65) Prior Publication Data

US 2016/0378964 A1    Dec. 29, 2016

(30) Foreign Application Priority Data

Jun. 29, 2015   (IN) ............................. 3294/CHE/2015

(51) Int. Cl.
| | | |
|---|---|---|
| G06F 21/32 | (2013.01) | |
| A61B 5/0205 | (2006.01) | |
| A61B 5/0402 | (2006.01) | |
| A61B 5/00 | (2006.01) | |
| A61B 5/117 | (2016.01) | |
| A61B 7/00 | (2006.01) | |

(52) U.S. Cl.
CPC ............ *G06F 21/32* (2013.01); *A61B 5/0205* (2013.01); *A61B 5/0402* (2013.01); *A61B 5/117* (2013.01); *A61B 5/4803* (2013.01); *A61B 5/7225* (2013.01); *A61B 5/7278* (2013.01); *A61B 7/003* (2013.01)

(58) Field of Classification Search
CPC ......... G06F 21/32; G06F 17/27; G10L 17/005
USPC ............................................... 340/5.52, 5.82
See application file for complete search history.

(56) References Cited

U.S. PATENT DOCUMENTS

| | | | | |
|---|---|---|---|---|
| 9,257,133 | B1* | 2/2016 | Strand ..................... | G06F 21/32 |
| 2005/0251056 | A1* | 11/2005 | Gribkov ............... | A61B 5/0452 600/509 |
| 2009/0232361 | A1* | 9/2009 | Miller ................ | G06K 9/00892 382/115 |
| 2010/0153470 | A1* | 6/2010 | Angell .................... | G06F 21/32 707/803 |
| 2011/0077946 | A1* | 3/2011 | Shectman ............. | G10L 17/005 704/270 |
| 2014/0085050 | A1* | 3/2014 | Luna .................. | G07C 9/00087 340/5.82 |
| 2014/0120876 | A1* | 5/2014 | Shen .................. | A61B 5/04525 455/411 |
| 2014/0143064 | A1 | 5/2014 | Tran | |
| 2015/0068069 | A1* | 3/2015 | Tran ...................... | H04B 1/385 36/136 |

* cited by examiner

*Primary Examiner* — Thomas Alunkal
(74) *Attorney, Agent, or Firm* — Finnegan, Henderson, Farabow, Garrett & Dunner LLP

(57) ABSTRACT

In certain embodiments of the present disclosure relate to a method for detecting liveness of a user during biometric authentication. The method comprising identifying a speech signal in a pre-determined time interval associated with the speech signal. Furthermore, the method comprising determining a speech respiration co-occurrence (SRC) score associated with the speech signal. In addition, the method comprising detecting liveness of the user, if the SRC score is above a predefined threshold, wherein the detection of liveness further aids in increasing the security of biometric authentication system.

20 Claims, 4 Drawing Sheets

SYSTEM AND METHOD FOR DETECTING LIVENESS DURING BIOMETRIC AUTHENTICATION

PRIORITY CLAIM

This U.S. patent application claims priority under 35 U.S.C. §119 to India Application No. 3294/CHE/2015, filed Jun. 29, 2015. The entire contents of the aforementioned application are incorporated herein by reference.

TECHNICAL FIELD

This disclosure relates generally to biometric authentication. More specifically, it relates to a system and method for detecting liveness during biometric authentication.

BACKGROUND

Biometric authentication is an attractive replacement for traditional password based authentication scenarios. Over the years, this authentication technique is widely used for authenticating access to physical setup as well as digital data. However, it has been observed that with the advancement in digital electronics and computer systems fraudsters could still gain access to high security area by simulating the signals generated from many of the physiological parameters that are finally used for the authentication. For example, one of the biometric signals that is often used for authentication is ECG which has a unique signature component for a person. Another example is adding voice based authentication. It is much easier to playback audio recordings or may be imitate a particular voice to pass through an authentication system. A number of other factors of authentication can be added to such system such as face, iris, finger print, etc. But all of these methods can be susceptible to the playback attack and different methods of liveness checking specific to the input type have been a challenge in detecting the fraudsters.

SUMMARY

Certain embodiments of the present disclosure relate to a method for detecting liveness of a user during biometric authentication. The method comprising identifying a speech signal of the user in a pre-determined time interval. Furthermore, the method comprising determining a speech respiration co-occurrence (SRC) score associated with the speech signal. In addition, the method comprising detecting liveness of the user, if the SRC score is above a predefined threshold.

Certain embodiments of the present disclosure also relate to a system for detecting liveness of a user during biometric authentication. The system comprises at least one processor and a computer-readable medium storing instructions that, when executed by the at least one processor, cause the at least one processor to identify a speech signal in a predetermined time interval associated with the speech signal. Furthermore, the system comprises at least one processor and the computer-readable medium storing instructions that, when executed by at least one processor, cause at least one processor to determine a speech respiration co-occurrence (SRC) score associated with the speech signal. In addition, the system comprises at least one processor and the computer-readable medium storing instructions that, when executed by the at least one processor, cause at least one processor to detect liveness of the user, if the SRC score is above a predefined threshold.

Certain embodiments of the present disclosure also relate to a non-transitory, computer-readable medium storing instructions that, when executed by a processor device, cause the processor device to perform acts of identifying a speech signal in a predetermined time interval associated with the speech signal. Furthermore, the non-transitory, computer-readable medium storing instructions that, when executed by the processor device, cause the processor device to perform acts of determining a speech respiration co-occurrence (SRC) score associated with the speech signal. In addition, the non-transitory, computer-readable medium storing instructions that, when executed by the processor device, cause the processor device to perform acts of detecting liveness of the user, if the SRC score is above a predefined threshold.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Herein, the method to detect the liveness of the physiological or biometric signal is proposed. Proposed method adds an additional step or a first stage verification of the 'liveness' of a subject/user from whom the biometric signal is being originated and then on successful authentication of the 'liveness' passes the authentication flow to the next stage. This concept is well explained in conjunction with the FIG. 1-FIG. 4.

Figure 1:
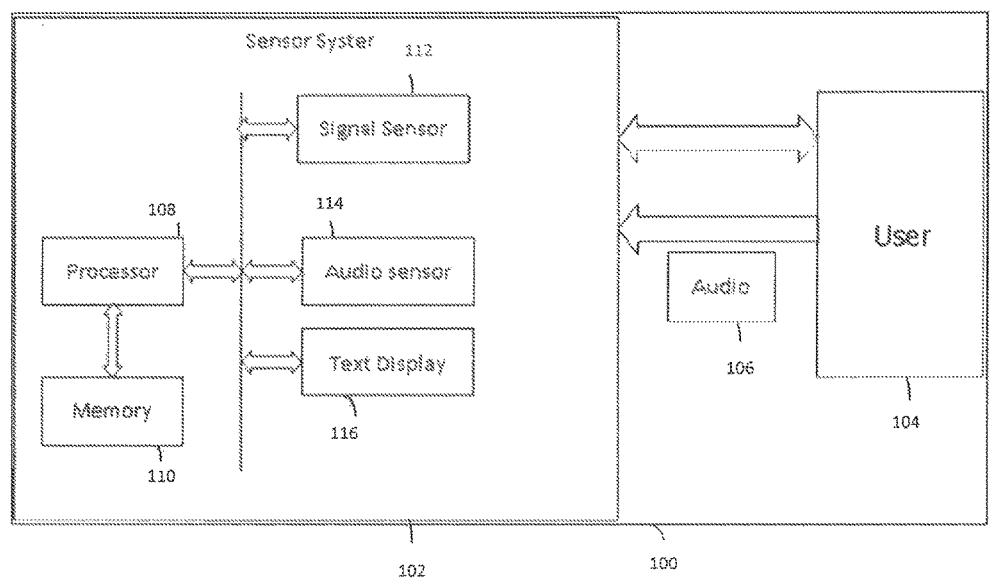
FIG. 1 illustrates an exemplary overview of a system for detecting liveness during biometric authentication, according to some embodiments of the present disclosure.

FIG. 1 illustrates an exemplary overview of a system 100 for detecting liveness during biometric authentication, according to some embodiments of the present disclosure. The system includes a sensor system 102 and a user device 104 electronically communicating via an audio channel 106. The sensor system 102 includes a processor 108 electronically communicating with a memory 110. The sensor system 102 includes a signal sensor. The sensor system 102 further includes an audio sensor 114 and a text display device 116. The signal sensor 112, the audio sensor 114 and the text display 116 are electronically communicating with the processor 108.

The signal sensor 112 is capable of detecting biometric signals from the user of the user device 104. The audio sensor 106 is capable of detecting audio/speech signal inputs from the user. The text display device 116 is capable of displaying randomly generated texts that is to be spoken by the user. The processor 108 centrally processes the programs running for sensor data acquisition and processing. The memory 110 stores programs that are run by the processor 108.

In some embodiments, the system 100 uses the correlation between speech and respiration signal to provide a speech respiration co-occurrence (SRC) score which is used as a liveness metric for biometric based authentication. The term liveness used herein is to describe a live instance/event/actual presence of a subject who will be authenticated biometrically. The embodiment uses electrocardiogram (ECG) signal as the dependent physiological biometric parameter. The system 100 requires audio and respiratory signals of the user generated via the user device 104. The respiration signal of the user can be obtained in two ways. First one is by using the change in impedance of the body (bio-impedance) and second is by deriving respiration signal from ECG signal, which is called ECG Derived Respiration (EDR).

In one example the speech has an effect on the respiration signal of the user. To produce audible speech, one inspires, holds their breath and then talks during the expiration. When needed, another inspiration occurs and talking continues. The inhalation of air increases the volume of the lungs and hence the impedance. More impedance means more amplitude of the respiration signal. So as the user exhales while speaking, the respiration signal has a downward slope. This characteristic of the respiration signal when coinciding with speech is proposed as a measure termed bio-impedance liveness of the user.

The system 100 is thus robust against playback attacks. In this invention, the system 100 randomly generates a phrase which ensures that the amount of time a person would be speaking is of dynamic duration. This will make it extremely difficult for a simulator device to spoof the system. By determining the liveness of the user, the system 100 will be able to increase the robustness of authentication based on ECG or other physiological signals.

In some embodiments, the system 100 performs the following: The audio signal of the user captured from the microphone of any device or the user device 104. The system 100 captures single lead ECG signal of the user from dry electrode which may be in contact with the user finger tips or a wearable sensor. The wearable sensor may be attached to the user device 104. The same lead may also be used for acquiring the bio-impedance which gives the respiration signal. The liveness will be measured in terms of the SRC score which would identify between living and non-living subject (example, a simulator which can be used for spoofing).

FIG. 1 is well explained below with an example:
Considering a data is coming from the user device 104 generated by the user of the user device 104 and the user intends to authenticate himself. As the user sends the ECG signal to the sensor system 102 in conjunction with signal sensor 112, its respiration signal is calculated using either bio-impedance based respiration or ECG derived respiration. The user is prompted by the text display 116 to speak up a phrase. As the user speaks, an audio signal is received by the audio sensor 114. The processor 108 and memory 110 identify the time interval associated with the speech signal detected by audio sensor 114. The time interval herein is a predetermined time interval. For the duration of the speech signal, the respiration signal is analyzed. The slope of the respiration signal for that duration is measured and the SRC score is calculated. If the SRC score is above the predefined threshold, the user is detected as live. The ECG signal captured during the interval associated with the speech signal detected by the audio sensor 114 is then used for determining the biometric authentication of the user 104.

Another example wherein the detection is successful in identifying a spoof. As described below:
The user intends to authenticate himself. As the user sends the ECG signal to the sensor system 102 in conjunction with signal sensor 112, its respiration signal is calculated using either bio-impedance based respiration or ECG derived respiration. The user is prompted by the text display 116 to speak up a phrase. As the user speaks, audio signal is received by the audio sensor 114. The processor 108 and memory 110 identify the time interval associated with the speech signal detected by audio sensor 114. For the duration of the speech signal, the respiration signal is analyzed. The slope of the respiration signal for that duration is measured and SRC score is calculated. If the SRC score is below the predefined threshold, the user is detected as spoof. Thus, the ECG signal captured during the interval with the speech signal detected by the audio sensor 114 is not used for biometric authentication as the user 104 is detected as spoof.

Figure 2:
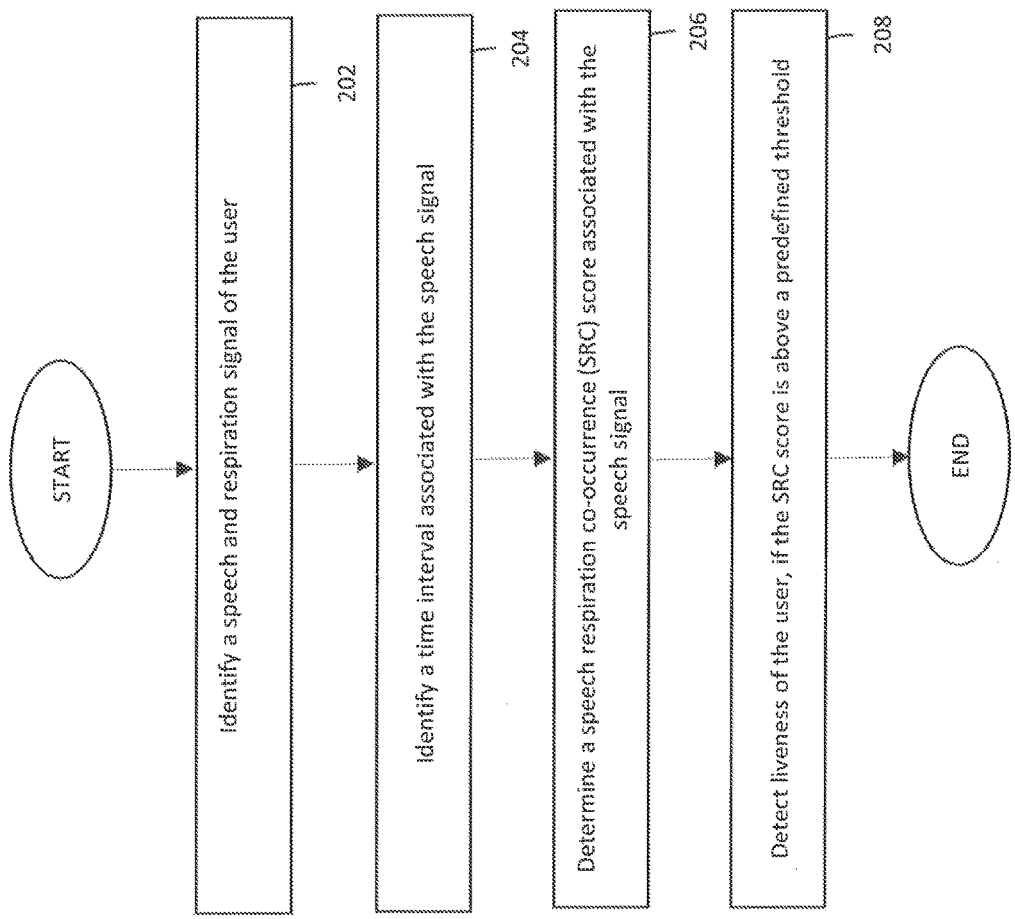
FIG. 2 is a flowchart of an exemplary method for detecting liveness during biometric authentication, according to some embodiments of the present disclosure.

FIG. 2 is a flowchart of an exemplary method for detecting liveness during biometric authentication, according to some embodiments of the present disclosure.

At step 202, a speech signal and a respiration signal of a user is identified.

In some embodiments, a voice signal or an audio signal, ECG and other biometric parameters from the user as inputs are received. For example, the user may be prompted, by a device which requires authentication, to speak dynamic text phrase audibly near the microphone of such device at the time when the user is seeking access. Such device applies the voice activity detector on the audio signal to get start and end time of the speech signal of the user. The device can be any electronic device, example a Laptop. The ECG signal, the respiration signal along with the audio signal are collected simultaneously for a sufficiently long time which can accommodate even slow speakers. The duration of receiving the signal is based on the random dynamic text generated. Also, depending upon the convenience and level of security the other biometric parameters could either be collected simultaneously along with the audio for the next stage processing or after the audio recording.

At step 204, a time interval associated with the speech signal is identified. For example, a start time interval may be t1 and an end time interval may be t2 of the speech signal. The duration between t1 and t2 may last for few seconds, within which the speech signal is analyzed and identified.

At step 206, a speech respiration co-occurrence (SRC) score associated with the speech signal is determined. An average slope s(t) of the respiration signal is determined for the duration of the speech signal.

In some embodiments, histogram of the slope values H(s) is computed. Further, the SRC is determined as below:

$$SRC=-\text{sign}(S_{max}+S_{min})*\max(H(s))/\text{variance}(H(s))$$

Wherein, sign( ) function is the signum function of the input parameter. $S_{max}$ and $S_{min}$ are the maximum and minimum slope of the respiration signal, respectively. For a positive liveness score the peak of H(s) will occur on the negative X-axis of the histogram H(s). This is well explained in conjunction with FIG. 3 and FIG. 4.

For example, the empirically derived parameters are—
Number of bins for the calculation of histogram of slope (H(s))=200 and
Predefined threshold value for SRC score=1;
From the slope of the respiration signal, we get $S_{max}$=6 and $S_{min}$=-8
Thus, calculating the histogram of the slope of the respiration signal:

$$(H(s)),\max(H(s))=136 \text{ and variance}(H(s))=98.744$$

Lastly, by substituting all the values as below the SRC score will be:

$$SRC=-\text{sign}(-2)*136/98.744=1.3773$$

Yet in another example, From the slope of the respiration signal, we get $S_{max}$=6 and $S_{min}$=-5;
Thus, calculating the histogram of the slope of the respiration signal:

$$(H(s)),\max(H(s))=210 \text{ and variance}(H(s))=230.81;$$

Lastly, by substituting all the values as below the SRC score will be:

$$SRC=-\text{sign}(1)*210/230.81=-0.9.$$

At step 208, liveness of the user is detected if the SRC score is above a predefined threshold. The detection of liveness further aids in biometric authentication of the user. If the SRC score is high positive value above the predefined threshold, then the subject is considered live. On detecting liveness of the subject is live, the authentication flow is passed onto the next stage of biometric authentication. Alternatively, on successful detection of liveness the complete authentication can take place wherein, the other biometric parameters have been simultaneously verified.

Referring back to previous example cited in step 206 wherein the SRC score is greater than the predefined threshold 1 i.e. 1.3773>1, it shall be considered as liveness is detected and thus the detection is successful in providing authentication.

If the SRC is lower than the predefined threshold, it is considered that the subject is not live and hence the authentication is rejected.

Referring back to the yet another example, wherein the SRC score is less than the predefined threshold 1 i.e. -0.9<1, it shall be considered that the liveness detection has failed.

Figure 3:
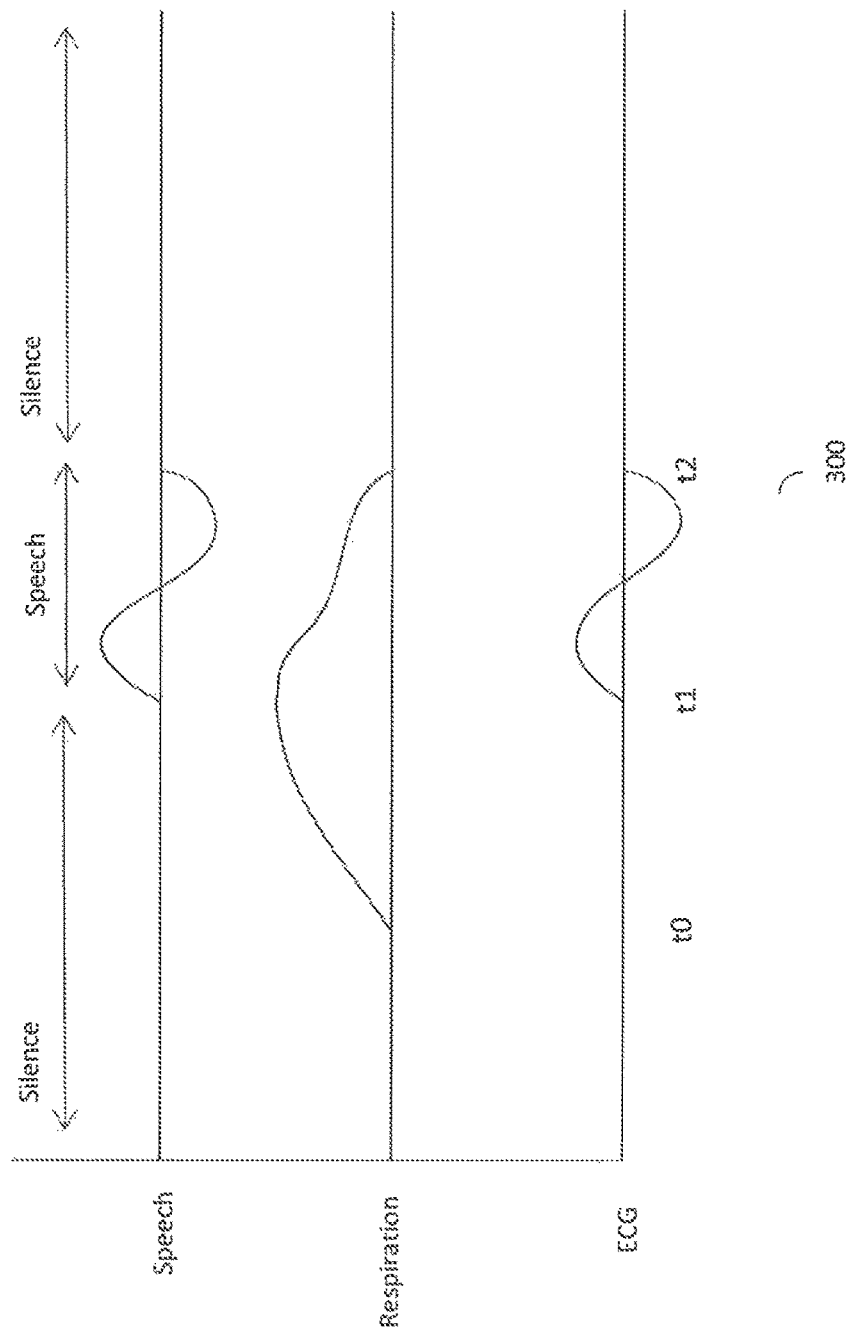
FIG. 3 is a graph illustrating the method for detecting liveness during biometric authentication, according to some embodiments of the present disclosure.

FIG. 3 is a graph 300 illustrating the method for detecting liveness during biometric authentication, according to some embodiments of the present disclosure.

The graph 300 is plotted in such a way that Y-axis refers to ECG signal, respiration signal and speech signal determined by the system 100 of a user who shall be tested for biometric authentication. The X-axis refers to time. Thus, the graph 300 is representing three graphical patterns simultaneously.

First graphical pattern shows time interval t0 to t1 as silence mode. This is when the system prompts the user to speak a few words. Then time interval t1 to t2 is when the speech signal by the user is identified by the device. Then from time interval t2 onwards it is silence mode again. Thus the first graphical pattern represents identification of the speech signal of the user in the time interval from t1 to t2.

The second graphical pattern represents the respiration signal captured during the time interval from t0 to t2. The respiration signal can be partitioned into inhalation and exhalation associated with the user. This is well identified in the time interval t0 to t1 indicating the inhale of the respiration and the time interval t1 to t2 indicating the exhale of the respiration. It is well observed in the second graphical pattern that during inhale, one is breathing in and thus the signal is increasing in its amplitude, whereas in exhalation the respiration signal is dropping down. The SRC shall be calculated based on the slope that is identified during the time interval t1 to t2.

Thus, the user inhales and starts speaking at t1 and completes the utterance at t2. During this interval the exhalation is shown by a decreasing pneumogram plot.

Thus, the average slope s(t) of the respiration signal is determined for the time interval t1 to t2 of the speech signal. The histogram of the slope values H(s) is also computed. Thus, giving a SRC score which will be compared with the predefine threshold. From the graph itself it is clear that the SRC score will be above the predefined threshold and thus the liveness of the user is detected.

$$SRC=-\text{sign}(S_{max}+S_{min})*\max(H(s))/\text{variance}(H(s))$$

Wherein, sign( ) function is the signum function of the input parameter. $S_{max}$ and $S_{min}$ are the maximum and minimum slope of the respiration signal, respectively. For a positive liveness score the peak of H(s) will occur on the negative X-axis of the histogram H(s).

In third graphical pattern, the ECG signal is determined throughout the time interval from t0 to t2 and beyond. However, only the ECG signal window during the time interval time t1 to t2 is tested post the liveness detection is successful and used for biometric authentication of the user.

Figure 4:
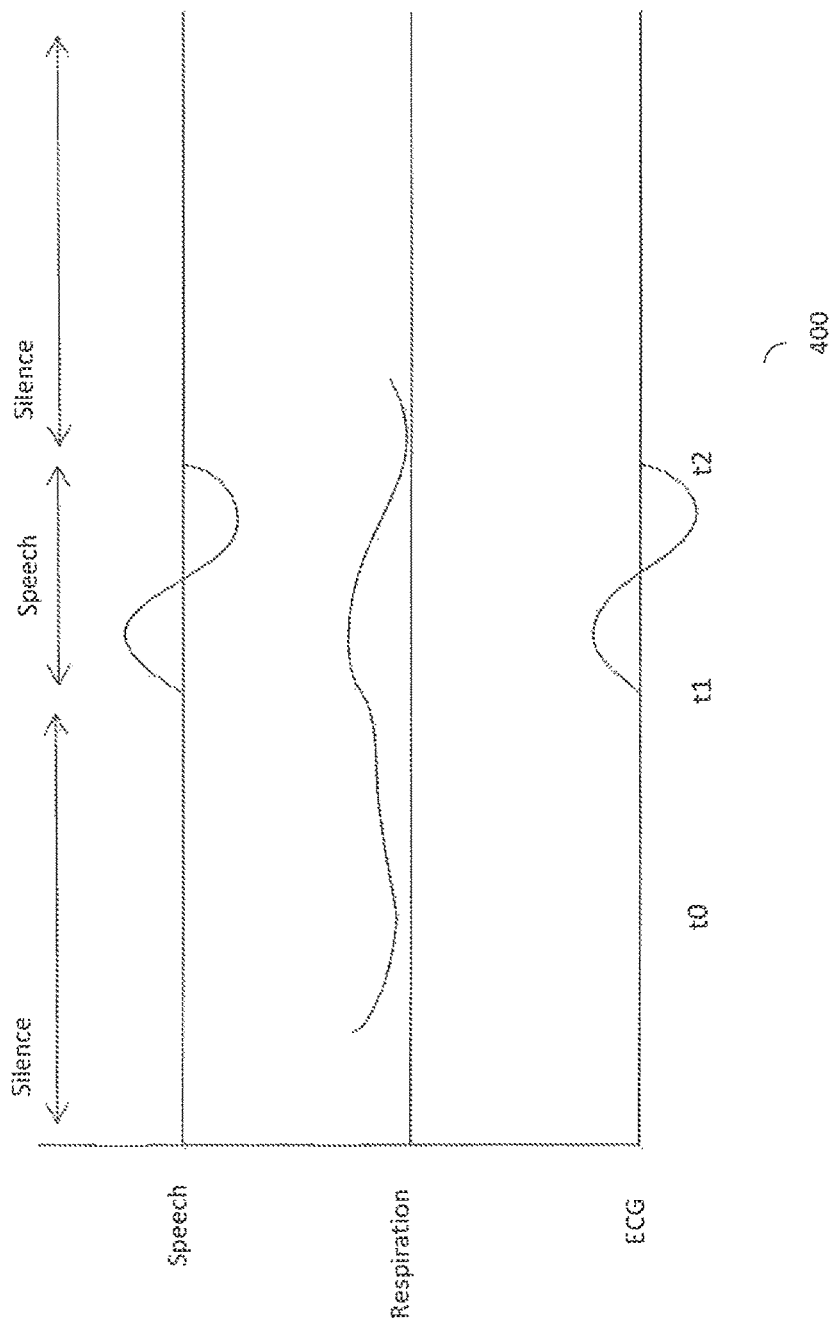
FIG. 4 is another graph illustrating the method for detecting liveness during biometric authentication, according to some embodiments of the present disclosure.

FIG. 4 is another graph illustrating the method for detecting liveness during biometric authentication, according to some embodiments of the present disclosure.

The graph 400 is plotted in such a way that Y-axis refers to ECG signal, respiration signal and speech signal determined by the system 100 of a user who shall be tested for biometric authentication. The X-axis refers to time interval. Thus, the graph 400 is representing three graphical patterns simultaneously.

First graphical pattern shows time interval t0 to t1 as silence mode. Then time interval t1 to t2 is when the speech signal is identified by the device which is detecting the speech signal. Then from time interval t2 onwards it is silence mode again.

Thus, the first graphical pattern represents identification of the speech signal in the time interval from t1 to t2.

The second graphical pattern represents the respiration signal captured during the time interval from t0 to t2. The respiration signal can be partitioned into inhale and exhale of the respiration of the user. This is well identified in the time interval t0 to t1 indicating the inhale of the respiration and the time interval t1 to t2 indicating the inhale again and then dropping down at a mid-point of t1 and t2. The second graphical pattern captured during the time interval t0 to t2 is unclear and uncertain. Thus, when the SRC is calculated for such patterns, the SRC score will be below the predefined threshold. Thus, indicating that the liveness test is failed. For example, the SRC is determined as below:

$$SRC=-\text{sign}(S_{max}+S_{min})*\max(H(s))/\text{variance}(H(s))$$

Wherein, sign( ) function is the sign of the input parameter. $S_{max}$ and $S_{min}$ are the maximum and minimum slope of the respiration signal, respectively. For a positive liveness score the peak of H(s) will occur on the negative X-axis of the histogram H(s).

In third graphical pattern, the ECG signal shall not be tested as the SRC score falls below determined throughout the time interval from t0 to t2 and beyond.

The specification has described systems and methods for detecting liveness during biometric authentication. The illustrated steps are set out to explain the exemplary embodiments shown, and it should be anticipated that ongoing technological development will change the manner in which particular functions are performed. Thus, these examples are presented herein for purposes of illustration, and not limitation. For example, steps or processes disclosed herein are not limited to being performed in the order described, but may be performed in any order, and some steps may be omitted, consistent with disclosed embodiments. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed:

1. A processor-implemented method for authenticating a user, comprising:
   generating a phrase;
   displaying the phrase to the user;
   after displaying the phrase to the user, collecting audio signal via an audio sensor and a signal comprising electrocardiogram (ECG) signal via a signal sensor for a first duration based on the displayed phrase;
   determining a respiratory signal based on the signal collected from the signal sensor;
   identifying, from the collected audio signal, a speech signal between a first time point and a second time point;
   determining a distribution of rates of changes of the respiratory signal between the first and second time points;
   determining a speech respiration co-occurrence (SRC) score based on the distribution of rates of changes of the respiratory signal;
   if the SRC score is equal to or above a predefined threshold, determining whether the user is authenticated based on the ECG signal collected between the first and second time points.

2. The method of claim 1, wherein the respiration signal is derived from the ECG signal.

3. The method of claim 2, further comprising: determining a slope sequence s(t) which is the derivative of the respiration signal.

4. The method of claim 3, further comprising, determining histogram of the slope sequence H(s) for the respiratory signal between the first and second time points.

5. The method of claim 4, wherein the SRC score is determined as:

$$SRC=-\text{sign}(S_{max}+S_{min})*\max(H(s))/\text{variance}(H(s)),$$

wherein sign ( ) is the signum function of the input parameter, $S_{max}$ and $S_{min}$ are the maximum and minimum slope of the respiration signal.

6. The method of claim 1, further comprising:
   determining the ECG signal as a spoof signal, if the SRC score is less than the predefined threshold; and
   indicating a failure of authentication.

7. The method of claim 1, wherein the phase is generated based on a random process.

8. The method of claim 1, further comprising:
   if the SRC score is below the predetermined threshold, determining not to provide the ECG signal for authentication of the user.

9. A system for authenticating a user, comprising:
   at least one processor in electronic communication with at least one traffic management device; and
   a computer-readable medium storing instructions that, when executed by the at least one processor, cause the at least one processor to:
   generate a phrase;
   display the phrase to the user;
   after displaying the phrase to the user, collecting audio signal via an audio sensor and a signal comprising electrocardiogram (ECG) signal via a signal sensor for a first duration based on the displayed phrase;
   determine a respiratory signal based on the signal collected from the signal sensor;
   identify, from the collected audio signal, a speech signal between a first time point and a second time point;
   determine a distribution of rates of changes of the respiratory signal between the first and second time points;

determine a speech respiration co-occurrence (SRC) score based on the distribution of rates of changes of the respiratory signal;

if the SRC score is equal to or above a predefined threshold, determine whether the user is authenticated based on the ECG signal collected between the first and second time points.

10. The system of claim 9, wherein the respiratory signal is derived from the ECG signal.

11. The system of claim 10, wherein the computer-readable medium storing instructions that, when executed by the at least one processor, further cause the at least one processor to:

determine an slope sequence s(t) which is the derivative of the respiration signal.

12. The system of claim 11, wherein the computer-readable medium storing instructions that, when executed by the at least one processor, further cause the at least one processor to:

determine histogram of the slope sequence H(s) for the respiratory signal between the first and second time points.

13. The system of claim 12, wherein the SRC score is determined as:

SRC score=$-\text{sign}(S_{max}+S_{min})*\max(H(s))/\text{variance}(H(s))$, wherein sign ( ) is the signum function of the input parameter, $S_{max}$ and $S_{min}$ are the maximum and minimum slope of the respiration signal.

14. The system of claim 9, wherein the computer-readable medium storing instructions that, when executed by the at least one processor, further cause the at least one processor to:

determine the ECG signal as a spoof signal, if the SRC score is less than the predefined threshold; and indicate a failure of authentication.

15. The system of claim 9, wherein the phrase is generated based on a random process.

16. The system of claim 9, wherein the computer-readable medium storing instructions that, when executed by the at least one processor, further cause the at least one processor to:

if the SRC score is below the predetermined threshold, determine not to provide the ECG signal for authentication of the user.

17. A non-transitory computer readable medium including instructions stored thereon that when processed by a hardware processor of a computer cause the computer to perform a method of authenticating a user, the method comprising:

generating a phrase;

displaying the phrase to the user;

after displaying the phrase to the user, collecting audio signal via an audio sensor and a signal comprising electrocardiogram (ECG) signal via a signal sensor for a first duration based on the displayed phrase;

determining a respiratory signal based on the signal collected from the signal sensor;

identifying, from the collected audio signal, a speech signal between a first time point and a second time point;

determining a distribution of rates of changes of the respiratory signal between the first and second time points;

determining a speech respiration co-occurrence (SRC) score based on the distribution of rates of changes of the respiratory signal;

if the SRC score is equal to or above a predefined threshold, determining whether the user is authenticated based on the ECG signal collected between the first and second time points.

18. The method of claim 1, wherein the respiratory signal is derived from bio-impedance reflected from the signal collected from the signal sensor.

19. The system of claim 9, wherein the respiratory signal is derived from bio-impedance reflected from the signal collected from the signal sensor.

20. The method of claim 17, wherein the respiratory signal is derived from bio-impedance reflected from the signal collected from the signal sensor.

* * * * *